United States Patent [19]

Smith

[11] Patent Number: 5,482,055
[45] Date of Patent: Jan. 9, 1996

[54] METHOD FOR ASSESSING CANINE HIP DYSPLASIA

[75] Inventor: Gail K. Smith, Havertown, Pa.

[73] Assignee: The Trustees of the University of Pennsylvania, Philadelphia, Pa.

[21] Appl. No.: 146,870

[22] Filed: Nov. 1, 1993

[51] Int. Cl.$^6$ ..................................................... A61B 5/00
[52] U.S. Cl. ......................................................... 128/782
[58] Field of Search .................................. 128/774, 779, 128/782; 33/511, 512

[56] References Cited

U.S. PATENT DOCUMENTS 5,228,454  7/1993  Siegler ..................................... 128/782

FOREIGN PATENT DOCUMENTS 0733653  5/1980  U.S.S.R. ................................. 128/782

OTHER PUBLICATIONS

G. K. Smith, D. N. Biery & T. P. Gregor, New Concepts of coxofemoral joint stability and the development of a clinical stress radio graphic method for quantitating hip joint laxity in the dog, Journal of the American Veterinary Medical Association, vol. 196, No. 1, pp. 59–70 (1990).
S. J. Heyman, M. A. Cofone & G. K. Smith, A Biomechanical Study of the Relationship of Coxofemoral Positioning to Passive Hip Joint Laxity in the Dog, Veterinary Surgical Journal, Sep.–Oct. 1992, p. 392.
"Hip Dysplasia", in James A. Baker Institute for Animal Health, Cornell Univesity, Annual Report 1988.

*Primary Examiner*—Max Hindenburg
*Attorney, Agent, or Firm*—James A. Drobile; Robert E. Rosenthal

[57] ABSTRACT

A method for determining the hip joint laxity of a dog includes the steps of positioning the hip joints of the dog, in a coordinate system having three degrees of freedom, a first degree of freedom for flexion and extension of the hip joint, a second degree of freedom for adduction and abduction of the hip joint, and a third degree of freedom for internal and external rotation of the hip joint, where a neutral position is defined as positioning of an axis of the femur perpendicular to a plane defined by both ischiatic tuberosities and both cranial dorsal iliac spines and where both femoral condyles are perpendicular to the long axis of the pelvis, between 10 degrees of flexion and 30 degrees of extension, between about 10 and about 30 degrees of abduction, and from about zero degrees of rotation to about 10 degrees of external rotation; applying a lateral outward force on the femoral head, the magnitude of the force being sufficient to cause the hip to enter a high stiffness region and, while maintaining the lateral outward force on the femoral head, obtaining a radiographic image of the hip.

9 Claims, 7 Drawing Sheets

METHOD FOR ASSESSING CANINE HIP DYSPLASIA

BACKGROUND AND FIELD OF THE INVENTION

This invention relates to veterinary techniques, and in particular to diagnostic techniques relating to hip joint disease dogs.

Canine hip dysplasia, CHD, is a common orthopedic disorder of dogs. The condition results in pain and discomfort in dogs, and reduces the mobility and useful working life of the dog. The problem of CHD is especially prevalent in purebred dogs. It has been suggested that the rate of CHD in the German Shepherd breed, for example, is anywhere from 23% to 69%. CHD afflicts guide dogs and other working dogs, as well as pets and show dogs.

CHD has long suspected to be a heritable trait. However, CHD generally afflicts dogs later in life. As a result, at a relatively young breeding age, a dog may lack the hip joint discomfort and loss of mobility symptomatic of CHD, and have no radiographic evidence of CHD, but still be genetically predisposed to development of CHD later in life. As a result, diagnosis of CHD in dogs does not provide the breeding community with sufficient guidance on whether the offspring of a given dog of breeding age will have offspring that are genetically predisposed to CHD.

Consequently, it is desirable to develop a technique for determining in a dog of relatively young age, the likelihood such a dog will develop CHD later in life.

The use of radiographic techniques for diagnosing of CHD will require accurate reading of radiographs. Consequently, it is desirable to develop new tools to assist in the accurate reading of radiographs.

It is accordingly an object of this invention to provide an improved method for determination in a relatively young dog, of the later development of CHD.

It is also an object of this invention to provide an improved gauge for reading radiographs in the method of the invention.

Additional objects and advantages of the invention will become apparent from the detailed description of a preferred embodiment which follows.

SUMMARY OF THE INVENTION

A method for determining whether a dog between about 16 weeks and two years in age will develop canine hip dysplasia includes the steps of positioning the hip joints of a dog, in a coordinate system having three degrees of freedom, a first degree of freedom for flexion and extension of the hip joint, a second degree of freedom for adduction and abduction of the hip joint, and a third degree of freedom for internal and external rotation of the hip joint, where a neutral position is defined as positioning of an axis of the femur perpendicular to a plane defined by both ischiatic tuberosities and both cranial dorsal iliac spines and where both femoral condyles are perpendicular to the long axis of the pelvis, between about 10 degrees of flexion and 30 degrees of extension, between about 10 and 30 degrees of abduction and from about zero degrees of rotation to about 10 degrees of external rotation; simultaneously with the step of positioning, applying a substantially lateral outward force to each femoral head of the dog, the magnitude of the force applied being sufficient to reach a high stiffness region of the hip; while continuing to apply force to each femoral head obtaining a radiographic image of the hip; determining the displacement between the center of the acetabulum and the center of the femoral head relative to a reference corrected for image magnification and size of the dog, to obtain a normalized displacement, and, if the normalized displacement is less than a selected lower threshold, determining that the dog has a very low probability of developing canine hip dysplasia, and if the normalized displacement is greater than a selected upper threshold, determining that the dog has a high probability of developing canine hip dysplasia.

A method of determining the hip joint laxity of a dog includes the steps of positioning the hip joints of the dog, in a coordinate system having three degrees of freedom, a first degree of freedom for flexion and extension of the hip joint, a second degree of freedom for adduction and abduction of the hip joint, and a third degree of freedom for internal and external rotation of the hip joint, where a neutral position is defined as positioning of an axis of the femur perpendicular to a plane defined by both ischiatic tuberosities and both cranial dorsal iliac spines and where both femoral condyles are perpendicular to the long axis of the pelvis, between about 10 degrees of flexion and 30 degrees of extension, between about 10 and about 30 degrees of abduction, and from about zero degrees of rotation to about 10 degrees of external rotation, applying an outward lateral force on the femoral head, the magnitude of the outward force being sufficient to cause the hip to enter a high stiffness region, and while maintaining the force, obtaining a radiographic image of the hip.

A gauge for determining dimensions of features on an image includes a transparent body having opposite planar faces and a plurality of frusto-conical bores defined therethrough, a narrow opening of each of said bores being sufficiently large to permit passage of a point of a marking implement therethrough, and a plurality of arrays of circular markings, each array centered on one of the bores, the circular markings each having a different diameter, from a selected maximum to a selected minimum in a selected increment, the circular markings being arranged in the arrays so as to provide a minimum difference in diameter between the circular markings in anyone of the arrays, greater than the selected increment.

DETAILED DESCRIPTION OF A PREFERRED EMBODIMENT

Figure 1:
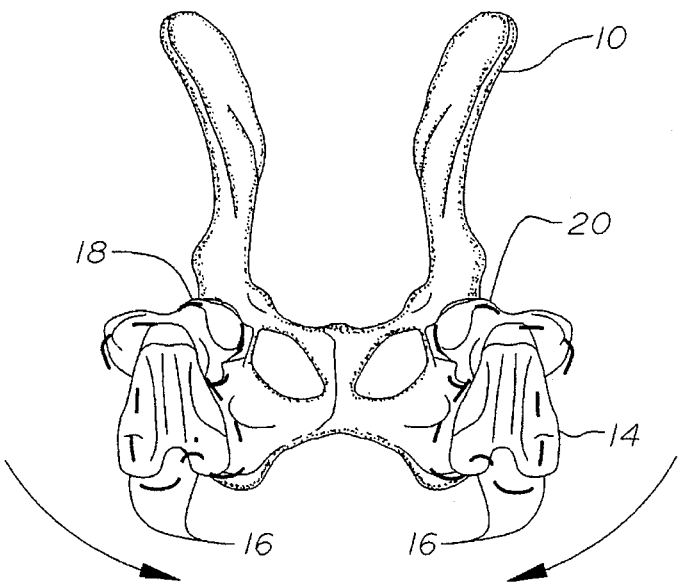
FIG. 1 is a ventrodorsal view of a skeletal canine pelvis and femur, illustrating the motion of the hip joint in the internal and external rotational axis.

By way of background, a coordinate system for the motions of the canine hip joint, or coxofemoral joint, will now be explained. With reference to FIG. 1 there is shown, a skeletal canine pelvis 10 and femurs 12 and 14. In FIG. 1, the hip joint is shown in a position of no internal or external rotation, no flexion or extension, and no adduction or abduction, relative to the plane of the pelvis. The position of no internal or external rotation, is defined by positioning of the femoral axis perpendicular to the plane of the pelvis, with the two femoral condyles 16 on each femur 12, 14 placed at a right angle to the long axis of the pelvis. The plane of the pelvis is defined by the two ischiatic tuberosities and both cranial dorsal iliac spines. The phantom lines in FIG. 1 show the position of the femurs after rotation in the direction of the arrows to roughly ten degrees of external rotation. As discussed below, the technique of the invention requires that the coxofemoral joint be positioned with between zero and 10 degrees of external rotation.

Figure 2:
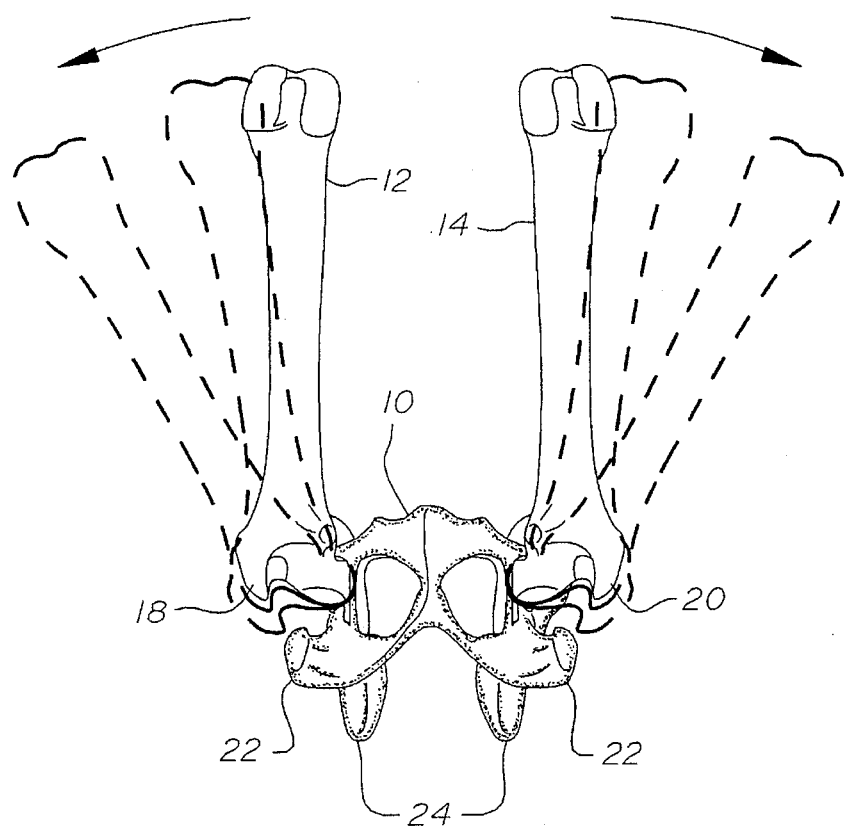
FIG. 2 is a rear (caudal) view of a skeletal canine pelvis and femur, illustrating the motion of the hip joint in the adduction and abduction axis.

Referring now to FIG. 2, the coordinate system of the hip joint will be further explained. FIG. 2 is a rear (caudal) view of the skeletal pelvis 10 and femurs 12 and 14 of a dog. In FIG. 2, the plane of pelvis 10 is depicted rotated approximately 15 degrees from horizontal. In this view, the ischiatic tuberosities 22 and the cranial dorsal iliac spines 24 are visible. The femurs 12, 14 are so positioned as in FIG. 1, that coxofemoral joints 18 and 20 are both in a position of no flexion or extension, no adduction or abduction, and no internal or external rotation. The position of the femurs 12, 14 shown in phantom, with the direction of motion shown by the arrows, illustrates abduction of the coxofemoral joints. As explained in more detail below, the practice of the technique according to the invention requires positioning of the coxofemoral joints between 10 degrees and 30 degrees of abduction.

Figure 3:
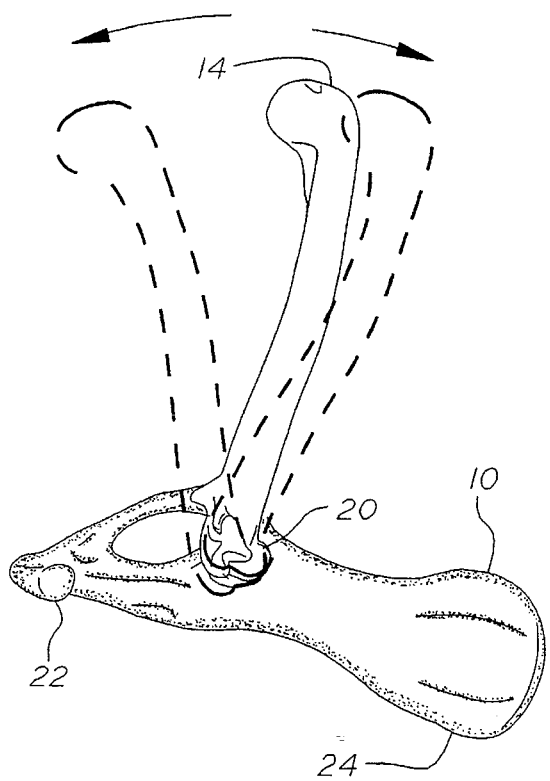
FIG. 3 is a side view of a skeletal canine pelvis and femur, illustrating the motion of the hip joint in the flexion/extension axis.

Referring now to FIG. 3, the coordinate system of the hip joint will be further explained. FIG. 3 is a side view of the skeletal canine pelvis 10 and femur 14. In FIG. 3, the plane of pelvis 10 is depicted rotated approximately 15 degrees from horizontal. Femur 14 is in the same position as in FIGS. 1 and 2. The phantom lines and the arrows illustrate flexion and extension of the hip joint. In the practice of the technique according to the invention, the hip joint must be positioned between 10 degrees of flexion, as indicated by the arrow pointing generally to the right (or clockwise) in FIG. 3, and the right-hand phantom representation of the femur, and 30 degrees of extension, as indicated by the arrow pointing generally to the left (or counterclockwise) and the left-hand phantom representation of the femur in FIG. 3.

Figure 4:
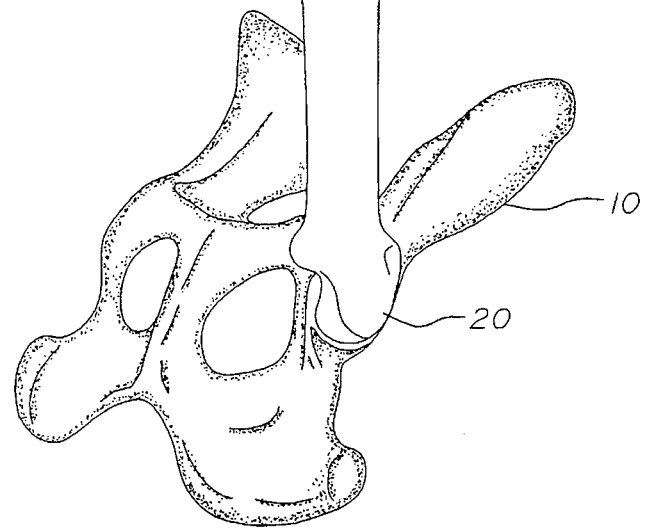
FIG. 4 is an isometric view of a skeletal canine pelvis and femur, showing the three degrees of freedom of the hip joint.

Referring now to FIG. 4, there is shown a skeletal dog pelvis 10 and a single femur 14. Femur 14 is in the same position as in FIGS. 1, 2 and 3. The three degrees of freedom, namely external and internal rotation, flexion and extension, and adduction and abduction, are illustrated by the arrows.

Figure 5:
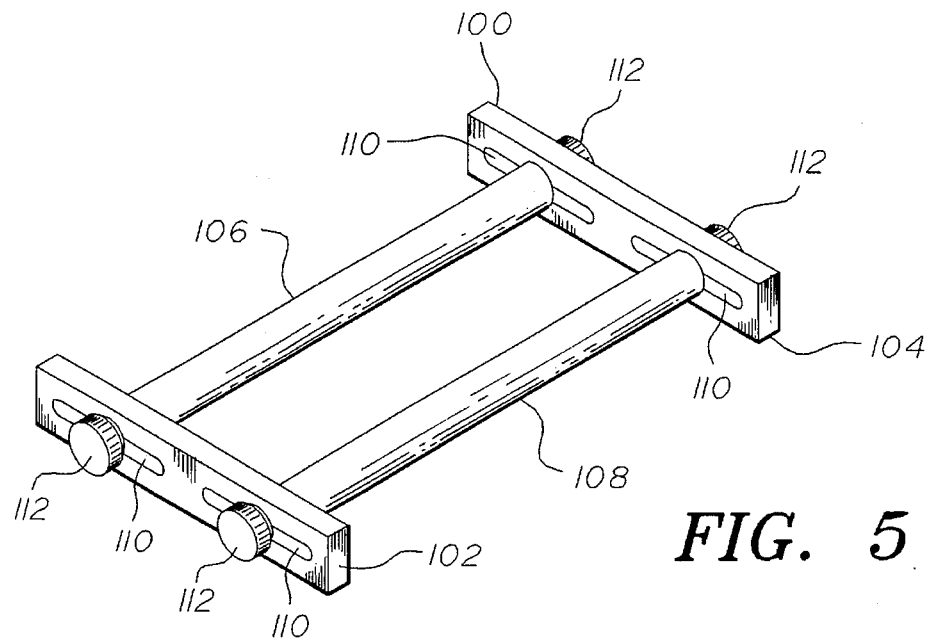
FIG. 5 is an isometric view of a distractor employed in the method of the invention.

Referring now to FIG. 5, there is shown a distractor 100 for use in a method according to the invention. Distractor 100 is employed for proper positioning of the coxofemoral joints of a dog in the procedure explained in more detail below. Distractor 100 has two parallel end members 102, 104, joined by two parallel rods 106, 108. The distance between rods 106, 108 is adjustable. As explained in detail below, it is necessary to adjust the distance between rods 106, 108 depending on the size of the dog, and in particular the distance between the two femoral heads of the dog. Two slots 110 are defined through each end member 100, 102, through which rods 106, 108 are attached. Slots 110 permit the distance between rods, 106, 108, to be adjusted. End caps 112 are provided at each end of each rod 106, 108, and may be loosened to permit lateral adjustment of rods 106, 108 relative to end members 110, and then tightened to prevent lateral translation of side members 106, 108, during use of distractor 100.

Rods 106, 108 must be X-ray transparent. By way of example, rods 106, 108 may be made of an acrylic. Rods 106, 108 may be covered in a padding material, such as a foam sleeve of the type sold for use as pipe insulation. End members 102, 104, may be of any suitable rigid material, such as aluminum. End caps 112 may be a unitary body having a threaded bore, into which a threaded shaft, which is inserted into the end of rods 106, 108, is engaged.

Figure 6:
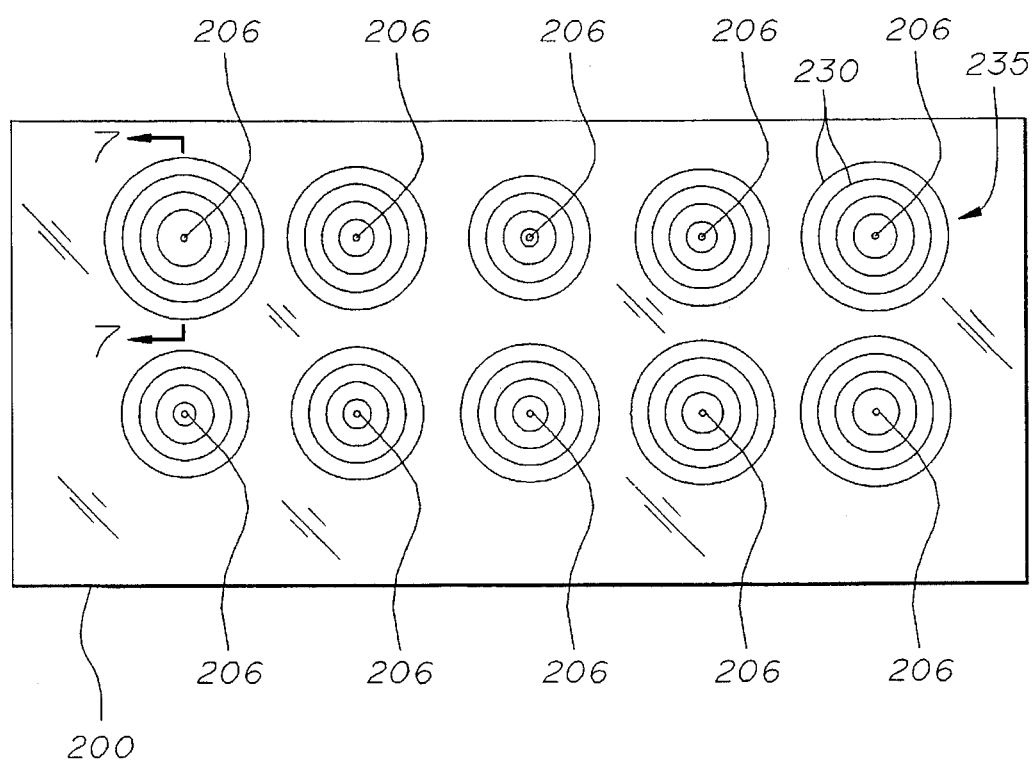
FIG. 6 is a top plan view of a circle gauge according to the invention.
Figure 7:
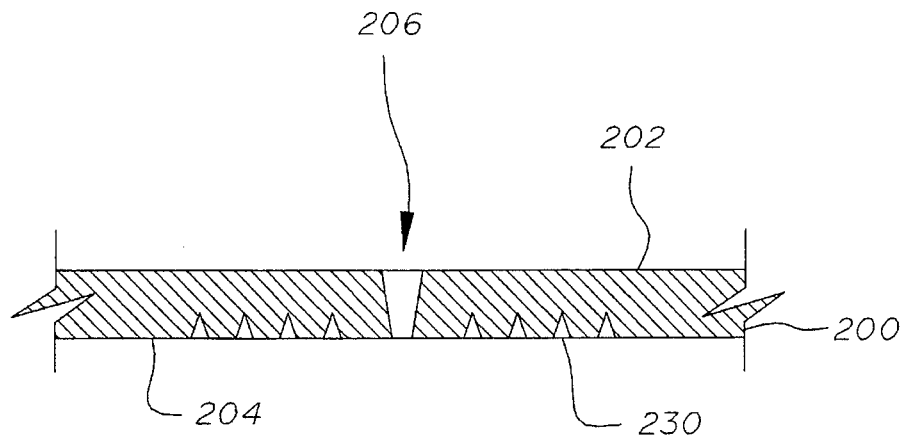
FIG. 7 is a partial sectional view of a circle gauge according to the invention, taken along line 7—7 of FIG. 6.

Referring now to FIGS. 6 and 7, there will be explained the structure of a circle gauge for use in a method of the invention. Circle gauge 200 is a thin, rigid transparent body having opposite parallel planar faces 202, 204. By way of example, circle gauge 200 may be of polycarbonate. There are defined through circle gauge 200 a plurality of frustoconical bores 206. While in the embodiment shown, there are 10 frustoconical bores, the number of bores may be varied. As shown in FIG. 7, each frusto-conical bore 206 has a wide opening in top face 202, and a narrow opening in bottom face 204, of circle gauge 200. The diameter of the narrow opening of bore 206, as shown for example in FIG. 7, is selected to be sufficiently wide to permit the point of a marking implement to be inserted therethrough. The diameter will be selected depending on the preferred writing implement with which circle gauge 200 is to be used. By way of example, with use of a mechanical pencil having a point 0.5 millimeters in diameter, it has been found satisfactory to provide an opening through bottom face 204 that is 0.7 millimeters in diameter.

Centered on each bore there is defined an array 235 of concentric circular markings 230. Circular markings 230 are optically-perceivable to the naked eye. Circular markings 230 are preferably as narrow as possible, while still being visible to the naked eye, to minimize obscuring of features on a radiograph on which the circle gauge 200 is placed. Preferably, each circular marking 230 is a score or groove defined in bottom face 204 of circle gauge 200. It has been found that the scores or grooves may be about 0.19 millimeters in width.

On gauge 200, there are preferably provided circular markings 230 of diameters varying at a selected increment from a minimum to a maximum. For example, in a preferred embodiment, there are 40 circular markings, from a minimum of 6 millimeters in diameter to a maximum of 45 millimeters in diameter, at an increment of 1 millimeter. The circular markings in any one array are preferably in equal increments of diameters from one another and those increments are preferably as great as possible, consistent with providing a certain number of circular markings on each array. For example, the difference in diameter between adjacent circular markings on any single array may be 10 millimeters. Preferably, the radii of circular markings 230 are indicated on circle gauge 200.

It will be understood that a circle gauge according to the invention permits the distance between a centered point and another centered point on a radiograph to be determined accurately to a very high degree of precision. It is also advantageous in determining the center point and radius of any generally circular structure on a radiograph. It has been found that if each circular marking is centered on the same bore, it is difficult, if not impossible, to determine the distances, radii, and centers, precisely.

Figure 8:
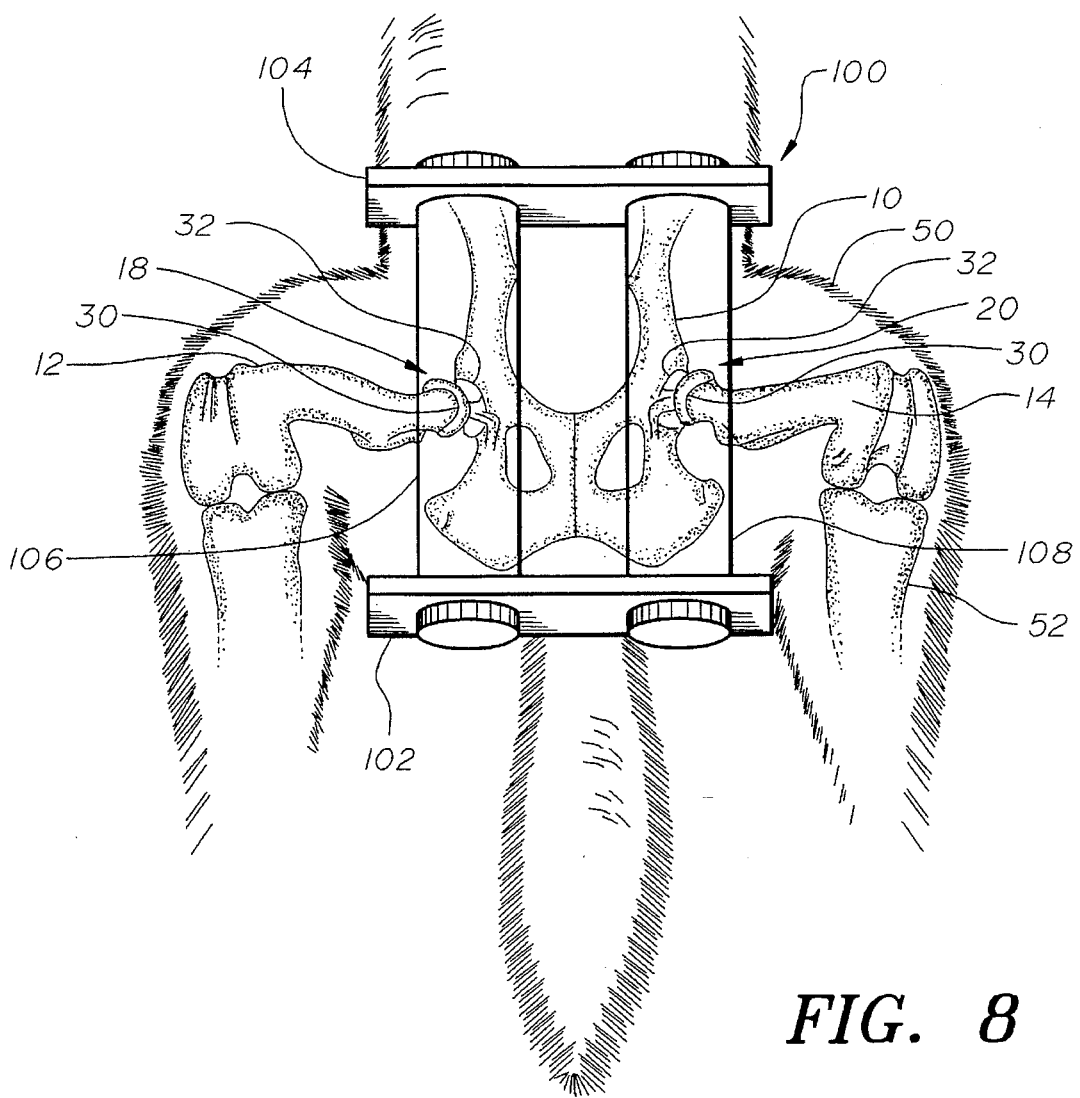
FIG. 8 is a partially-schematic view showing the placement of the distractor on the pelvic region of the dog in a process according to the invention, with the legs, tail, body, pelvis, femur and a portion of the tibia of the dog shown for illustrative purposes.

With reference to FIG. 8, the method for positioning the dog for obtaining a radiographic exposure in a method according to the invention will now be described. The dog is preferably sedated prior to obtaining the radiograph. In general, the dog must be sufficiently sedated that the musculature is relaxed and that there is no movement or response to the discomfort of the positioning procedure described below. In one acceptable sedation procedure, atropine sulfate, at 0.02 mg/kg body weight, diazepam, at 0.50 mg/kg body weight, and oxymorphone HCl, at 0.165 mg/kg body weight, are administered intravenously.

The compression view of the hip joint will now be explained. The radiograph obtained in the compression view is useful for comparison purposes, in reading radiographs of the distracted view. In order to obtain a compression view of the hips, the dog is placed in dorsal recumbency on a radiographic table in a plastic trough. In order to maintain the dog in position throughout the procedure, weights, such as sandbags, are preferably placed over the front legs and chest. The pelvis is preferably positioned with the primary x-ray beam centered over the midline between both hips. The hocks are grasped such that the tibias are parallel to the table surface and parallel to each other, and the stifles are in approximately 90 degrees of flexion. The femurs are approximately perpendicular to the table surface. More specifically, the femur is positioned so that, with respect to the coordinate system defined above, the hip position is between 10 degrees of flexion and 30 degrees of extension, between 10 degrees and 30 degrees of abduction, and between 0 and 10 degrees of external rotation. It will be noted that this coordinate system is with respect to the plane of the pelvis as defined above. In the dog, the plane of the pelvis is rotated approximately 15 degrees in the flexion/extension axis from the plane of the radiographic table. Once the femur is in this position, hand-held weights are placed lateral to the hips, and slight medial pressure is applied to the greater trochanters. While slightly rotating the hocks externally, the stifles are moved laterally, i.e., pushing outward against the weights, in an amount sufficient to avoid superposition of stifles on the hips, but not greater than the normal stifle spacing during stance-phase of weight bearing. The combination of these steps results in the application of a compressive force on the hip joint. The compressive force is maintained for an interval sufficient to permit radiographic exposure.

The distraction radiographic view will now be described with reference to FIG. 8. The dog 50 is placed in dorsal recumbency on the radiographic table, preferably in a plastic trough. The pelvis 10 is positioned so that the primary x-ray beam is centered over the midline between the hips. The examiner grasps the hocks such that the tibias are parallel to the table surface and parallel to each other, and the stifles are in approximately 90 degrees of flexion. The femurs are positioned so that the hip joint is between 10 degrees of flexion and 30 degrees extension, between 10 and 30 degrees of abduction, and from 0 to 10 degrees of external rotation. Within this range of positioning, it has been found by the inventor, the mean percentage of maximal hip laxity will be greater than 90 percent. It is preferred that the hip joint position be about 10 degrees externally rotated, in about 10 degrees of extension and about 20 degrees of abduction. At this position, maximal hip laxity is observed. This may be accomplished by grasping the hocks such that the tibias are parallel to the table surface and parallel to each other, and the stifles are in about 90 degrees of flexion with the femur perpendicular to the table. It will be noted, as before, that the plane of the table is rotated about 15 degrees in the flexion/extension axis, from the plane of the pelvis. Once the hip joint is in that position, a substantially lateral outward force, or distractive force, is applied to each femoral head 30. In a preferred technique, this is accomplished by applying an inward force near the knee and rotating each femur 12, 14 about a point intermediate the femoral head 30 and the knee, thereby forcing femoral head 30 outward.

Figure 9:
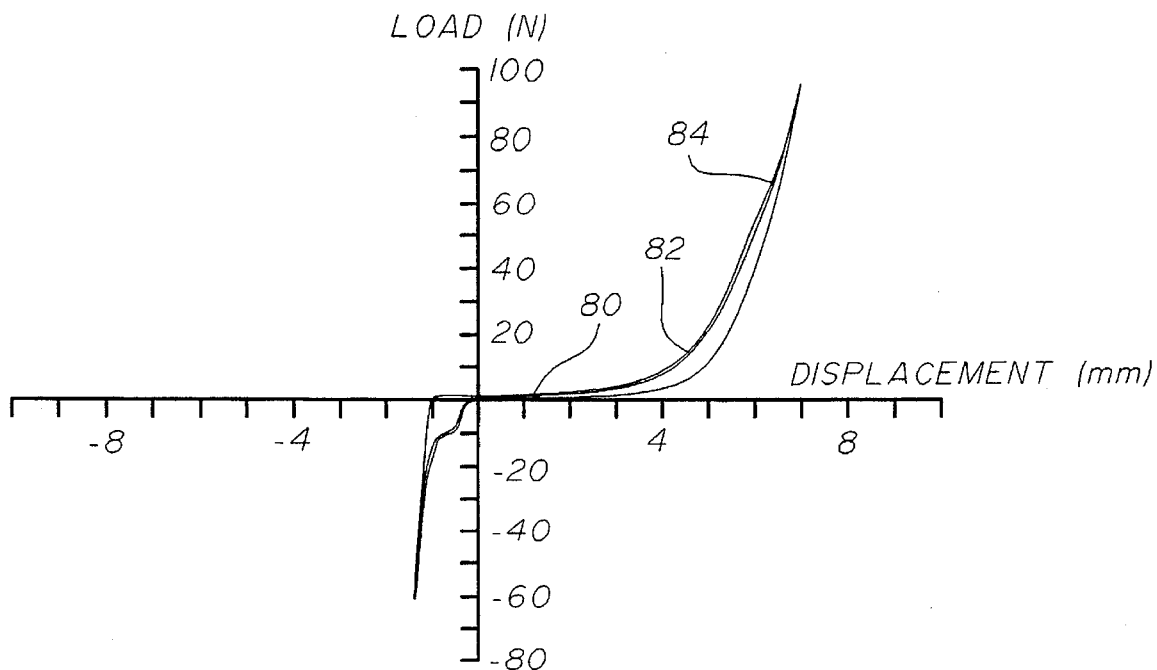
FIG. 9 is a graph showing load vs. displacement qualitatively in the canine hip.
Figure 14:
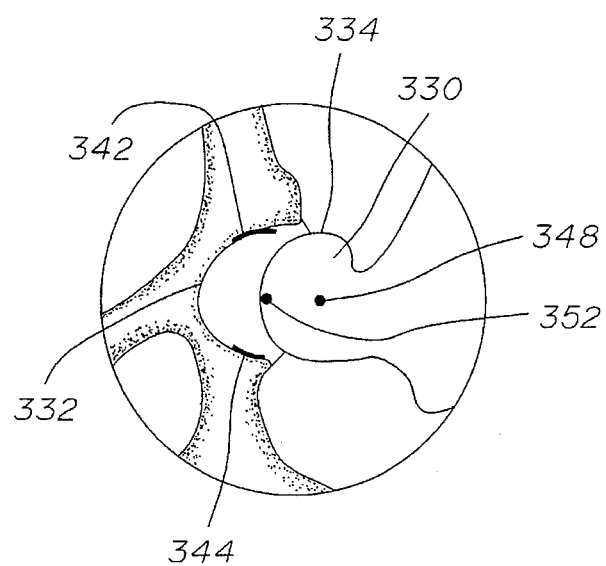
FIG. 14 is an enlargement of the indicated portion of FIG. 13.
Figure 10:
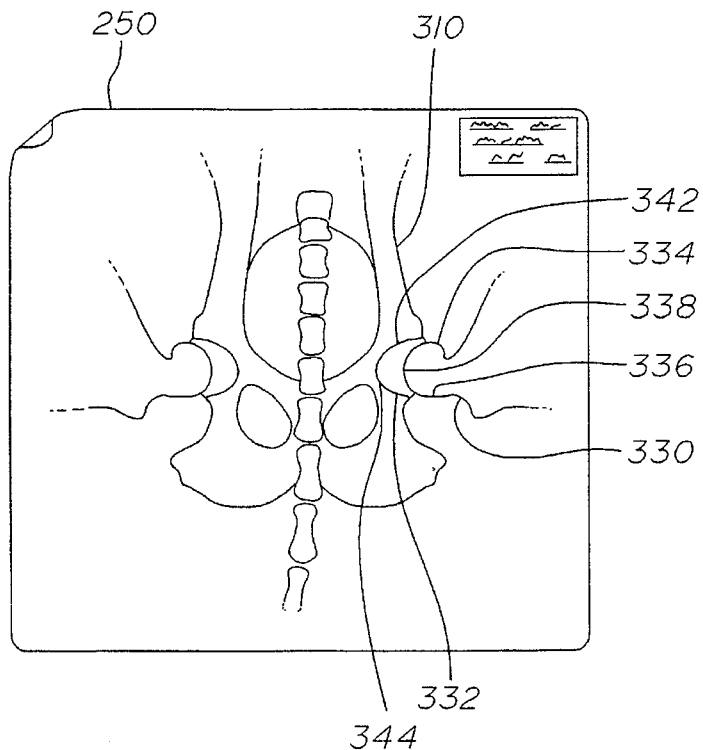
FIG. 10 is a partially-schematic representation of a radiographic image obtained in a method according to the invention.

It has been discovered by the inventor that motion of the canine femoral head relative to the center of the canine acetabulum can be described as a biological constraint having two phases. Referring to FIG. 9, which shows the load in newtons required to effect a given displacement in millimeters of the femoral head from the acetabulum, in studies conducted by the inventor on dog cadaver hips, there is a low stiffness region 80, a high stiffness region 84, and a transition region 82. In low stiffness region 80, the femoral head moves relatively far for a given applied load. In high stiffness region 84, the additional load required to effect a given increase in displacement is relatively great. In transition region 82, the additional load required to effect a given increase in displacement increases from the low end of transition region 82 to the high end thereof.

It has been discovered that the lateral outward force applied on the femoral head must be sufficient to reach high stiffness region 84. The examiner who is applying the distractive force will be able to detect the increasing resistance to the applied force. The threshold force has been discovered by the inventor to be at least 15 newtons, in dog cadavers, and is believed to be higher in live dogs. If an excessive additional force, of approximately 55 newtons, is applied, cavitation of the synovial fluid in the hip joint will occur, which will render the results of the procedure unreliable. The proper threshold force is maintained until the radiographic exposure has been completed which takes less than 2 seconds.

In a preferred technique, distractor 100 is placed between the rear legs, with the rearward end member 102 positioned slightly rearward of the pelvis 10 of the dog. The distance between the rods 106, 108, is preferably approximately equal to the distance between the femoral heads 30 of the dog. An evenly distributed downward force is applied on each end member 102, 104, of distractor 100. The force on the end members 102, 104 is sufficient to stabilize the position of pelvis 10. During distraction, the femoral heads 30 are forced laterally outward from the acetabulae. This is accomplished with the dog in the position illustrated in FIG. 8, by applying an inward force to the stifles 52. The point where the dog's leg contacts the distractor rod 108 is the point where the femur is fixed. The distractor rod 108 acts as a fulcrum, to facilitate applying the lateral outward or distractive force on femoral head 30. A preliminary distraction procedure should verify whether the stifles are moved so close together as to be superimposed on the hips during radiographic exposure. If the stifles are moved so close, then the position of distractor rods 106, 108, should be adjusted.

In a preferred embodiment of the exposure technique, a fast detail 400 speed rare earth ultraviolet film/screen system may be employed. By way of example, for a dog's pelvis measuring 15 centimeters in thickness, desirable settings would be 10 mAs and 78 kVp. A film-screen system of at least 400 is preferred.

Figure 11:
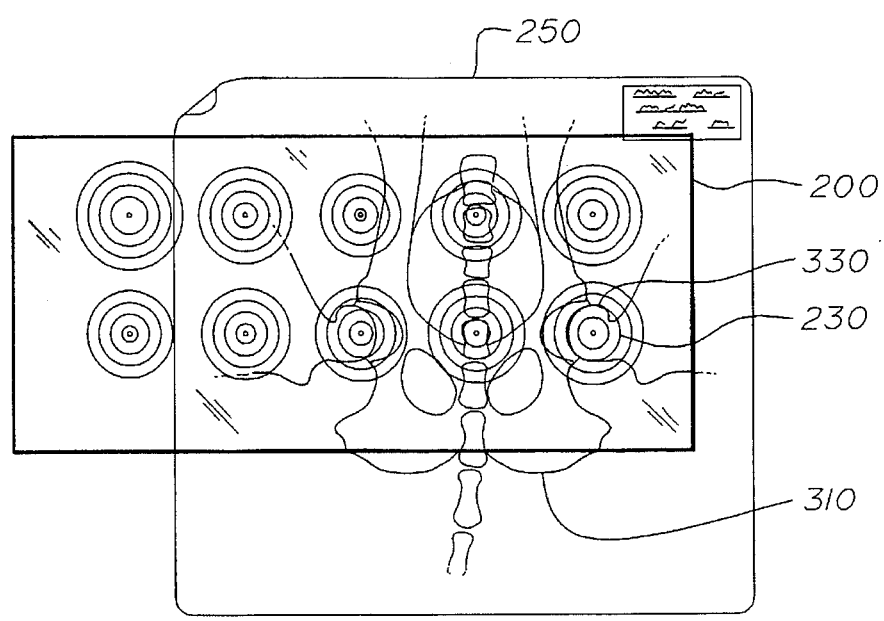
FIG. 11 is a top plan view of a circle gauge according to the invention superimposed on a partially-schematic view of a radiographic image obtained in a method according to the invention.

Referring now to FIGS. 10, 11, 12, 13, and 14, the method of reading a radiographic image 250 obtained according to the above-described method in order to evaluate hip joint laxity and the likelihood of the dog developing CHD will be described. This step includes determining the displacement between the center of the acetabulum and the center of the femoral head, relative to a reference corrected for image magnification and the size of the dog. The center of the image 330 of femoral head 30, and the diameter of the image 330 of femoral head 30, are preferably ascertained first. The center and diameter of femoral head image 330 are determined preferably by placing circle gauge 200 on radiographic image 250. A circular marking 230 of proper size is selected that contours as precisely as possible to the image 334 of the cranial edge and image 336 of the caudal edge of femoral head 30. It is important to note that the overlay of the circular marking to image 338 of the medial edge of femoral head 30 is not relevant. The step of fitting of a circular marking 230 of circle gauge 200 on the image of femoral head 30 on radiograph 250 is shown in FIG. 11. The center point 348 of femoral head image 330 is marked by placing a marking point through the bore at the center of the selected circular marking. The femoral head radius is recorded.

The next step is the determination of the center point of the image 332 of the acetabulum. A circular marking is selected from circle gauge 200 which can be positioned simultaneously to bisect the image of the radiodense subchondral bone at the image 342 of the craniomedial portion and the image 344 of the caudal portion. These images may best be seen in FIG. 14. It has been found useful, for correct placement of circle gauge 200, to refer to a radiographic view taken with the dog in the same position, but a compressive force applied on the femoral head, rather than a distractive force.

Figure 12:
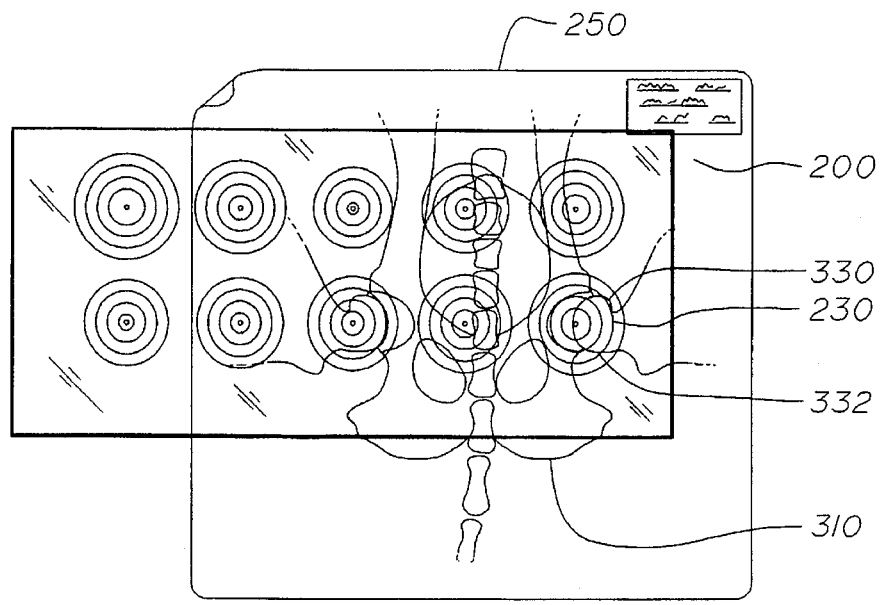
FIG. 12 is a top plan view of a circle gauge according to the invention superimposed on a partially-schematic view of a radiographic image obtained in a method according to the invention.
Figure 13:
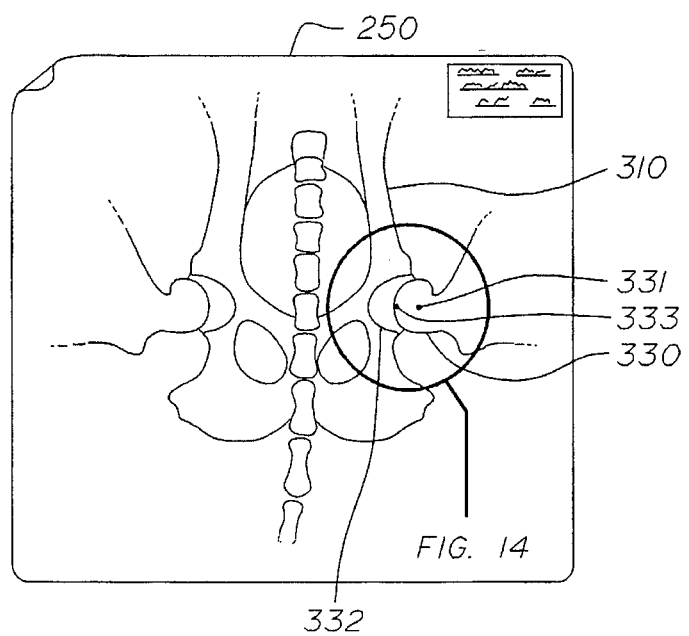
FIG. 13 is a partially-schematic view of a radiographic image obtained in a method according to the invention, showing marking of the femoral and acetabular centers.

Referring to FIG. 12, once circle gauge 200 is properly positioned on the acetabular landmarks, namely the craniomedial image 342 and caudal image 344, the center 352 of the image of the acetabulum is marked by placing a marking implement through the central bore.

The method is then repeated with respect to the other hip joint.

A distraction index, which is corrected for magnification of the radiographic image, and the size of the dog, may then be calculated. The distraction index may be obtained by dividing the distance between the center point 348 of the femoral head image and the center point 352 of the acetabulum image by the radius of the femoral head image. This calculation yields a dimensionless number.

The value of the distraction index can be employed to determine whether a dog is likely to develop canine hip dysplasia later in life. It has been discovered by the inventor that if the distraction index is less than a breed-specific selected lower threshold, then the diagnosis will be that the dog has a likelihood of less than 5% of developing CHD. This lower threshold has been found, in a study by the inventor, to be about 0.3 in German Shepherd dogs, and somewhat higher, about 0.4, in other breeds evaluated in the study. If the distraction index is greater then a breed-specific selected upper threshold, the dog is likely, with at least a 94 percent probability, to develop CHD. In the inventor's study, this upper threshold was found to be about 0.6 for German Shepherd dogs, and about 0.75, for a variety of other breeds.

Between the upper and lower breed-specific thresholds, the inventor has found that the likelihood of a dog developing CHD varies with the distraction index. The inventor has found that the technique of the invention is accurate in predicting the likelihood of a dog as young as four months in age developing CHD.

The method of the invention defined above is a reliable reproducible method of assessing the likelihood of a given dog developing CHD. The method may be employed on dogs as young as about 16 weeks with a reasonably high degree of accuracy.

This method has defined for the first time the acceptable ranges of positioning of the hip joint during radiographic exposure. It is also important to note that for the first time the amount of force to be applied to the femoral head to produce maximal lateral displacement has been accurately quantified.

It will be appreciated that there are considerable variations that can be accomplished in a method of the invention without departing from its scope. As a result, although a preferred embodiment of the invention has been described above, it is emphasized that the invention is not limited to a preferred embodiment and there exist other alternative embodiments that are fully encompassed within the invention's scope, which is limited only by the scope of the appended claims.

What is claimed is:

1. A method for determining whether a dog between about 16 weeks and two years in age will develop canine hip dysplasia, comprising the steps of:

(a) positioning the hip joints of the dog, in a coordinate system having three degrees of freedom, a first degree of freedom for flexion and extension of the hip joint, a second degree of freedom for adduction and abduction of the hip joint, and a third degree of freedom for internal and external rotation of the hip joint, where a neutral position is defined as positioning of an axis of the femur perpendicular to a plane defined by both ischiatic tuberosities and both cranial dorsal iliac spines and where both femoral condyles are perpendicular to the long axis of the pelvis, between about 10 degrees of flexion and 30 degrees of extension, between about 10 and about 30 degrees of abduction, and from about zero degrees of rotation to about 10 degrees of external rotation;

(b) simultaneously with said step (a), applying a substantially lateral outward force to each femoral head of the dog, the magnitude of said force being sufficient to reach a high stiffness region of the hip;

(c) while continuing to apply force as in said step (b), obtaining a radiographic image of the hip;

(d) determining the displacement between the center of the acetabulum and the center of the femoral head relative to a reference corrected for image magnification and size of the dog, to obtain a normalized displacement; and (e) if the normalized displacement is less than a selected lower threshold, determining that the dog has a very low probability of developing canine hip dysplasia, and if the normalized displacement is greater than a selected upper threshold, determining that the dog has a high probability of developing canine hip dysplasia.

2. The method of claim 1, wherein the force applied in said step (b) is not so large as to cause synovial fluid cavitation in the hip joint.

3. The method of claim 1, wherein said hip joint position is about 10 degrees externally rotated, in about 10 degrees of extension and about 20 degrees of abduction.

4. The method of claim 1, wherein said step of applying the force on the femoral heads comprises applying an inward force near the knee and rotating each femur about a point intermediate the femoral head and the knee.

5. The method of claim 1, wherein said step (d) comprises the step of determining the radius of the femoral head and the distance between the centers of the femoral head and of the acetabulum, on the radiographic image obtained in said step (c), and dividing the distance between the centers by the radius of the femoral head, to obtain the normalized displacement.

6. A method of determining the hip joint laxity of a dog, comprising the steps of:

(a) positioning the hip joints of the dog, in a coordinate system having three degrees of freedom, a first degree of freedom for flexion and extension of the hip joint, a second degree of freedom for adduction and abduction of the hip joint, and a third degree of freedom for internal and external rotation of the hip joint, where a neutral position is defined as positioning of an axis of the femur perpendicular to a plane defined by both ischiatic tuberosities and both cranial dorsal iliac spines and where both femoral condyles are perpendicular to the long axis of the pelvis, between about 10 degrees of flexion and 30 degrees of extension, between about 10 and about 30 degrees of abduction, and from about zero degrees of rotation to about 10 degrees of external rotation;

(b) applying a lateral outward force on the femoral head, the magnitude of said force being sufficient to cause the hip to enter a high stiffness region; and (c) while maintaining the force applied in said step (b), obtaining a radiographic image of the hip.

7. The method of claim 6, wherein the force applied in said step (b) is not so large as to cause synovial fluid cavitation in the hip joint.

8. The method of claim 6, wherein said hip joint position is about 10 degrees externally rotated, in about 10 degrees of extension and about 20 degrees of abduction.

9. The method of claim 6, wherein said step of applying the force on the femoral heads comprises applying an inward force near the knee and rotating each femur about a point intermediate the femoral head and the knee.

* * * * *